United States Patent [19]
Youssef

[11] 4,008,622
[45] Feb. 22, 1977

[54] METHOD OF TESTING THE QUALITIES OF A MATERIAL

[75] Inventor: Hassan Youssef, Taverny, France

[73] Assignee: La Metallurgie Francaise des Poudres Metafram, Paris, France

[22] Filed: May 29, 1975

[21] Appl. No.: 581,922

[30] Foreign Application Priority Data

June 13, 1974 France .............................. 74.20487

[52] U.S. Cl. .............................. 73/432 R; 73/61.2
[51] Int. Cl.$^2$ ........................................ G01N 33/20
[58] Field of Search ........... 73/53, 61.2, 86, 432 R, 73/64

[56] References Cited

UNITED STATES PATENTS

| | | | |
|---|---|---|---|
| 2,464,233 | 3/1949 | Hughes et al. ...................... | 73/86 X |
| 2,519,323 | 8/1950 | Shank et al. ........................... | 73/86 |
| 2,674,889 | 4/1954 | Toof ................................. | 73/432 R |
| 3,228,236 | 1/1966 | Landrum et al. ....................... | 73/86 |

*Primary Examiner*—Donald O. Woodiel
*Assistant Examiner*—Joseph W. Roskos
*Attorney, Agent, or Firm*—Haseltine, Lake & Waters

[57] ABSTRACT

In a method of testing a material to determine its suitability for forming at least a part of a self-lubricating bearing member containing oil by determining whether the material will cause deterioration of the oil, the material in powder form is immersed in the oil which is maintained for a period of time at a temperature at most equal to the maximum temperature of use of the oil, and the properties of the oil, e.g. viscosity and/or color, are compared with a sample of the oil maintained at the same temperature for the same length of time but which does not include the material.

7 Claims, No Drawings

METHOD OF TESTING THE QUALITIES OF A MATERIAL

The present invention relates to self-lubricating bearings.

Self-lubricating bearing-members, such as thrust-bearings or journal-bearings, have long been in use. These members are generally intended to support a rotating shaft and consist of a porous part which is generally obtained by sintering a metal powder and contains oil. It is known that lubrication is ensured by circulation of the oil contained in the journal-bearing, the oil being under pressure in the zone near to the application of the force exerted by the shaft and under reduced pressure in the other zones. Thus the journal bearing is lubricated continuously by the oil which it contains to start with and there is no renewal of the oil by external circulation.

In order to increase the capacities of self-lubricating journal-bearings and especially their working life and the loads which they can carry it has already been proposed in French Patent No. 1,377,414 to produce journal-bearings composed of two superimposed layers. The greater portion of the journal-bearing consists of a macroporous part which serves as an oil reservoir. The inner surface of this part which lies to the side to which the load is applied is coated with a microporous layer. This low-porosity layer opposes the circulation of the oil which tends to escape from the zone under pressure by re-entering the pores in the metal and thus increasing the bearing force of the shaft. However, the outer macroporous portion constitutes the oil reservoir in which the capillary forces are low and hence do not oppose the circulation of the oil.

In addition the diameter of the pores in the microporous layer is selected in such a way that, if at certain points in the macroporous portion the oil were completely pumped out, the capillary forces created in the fine pores of the inner layer would oppose penetration of air to the inside of the journal-bearing. Thus risks of seizure by penetration of air bubbles into the oil film are avoided and at the same time the bearing force of the bearing and its working life are increased.

However, for a bearing to work for a long time it is necessary that the oil should not deteriorate in time. This is particularly important in the case of self-lubricating bearing-members in which the amounts of oil brought into play are small and are not renewed.

Self-lubricating journal-bearings employed hitherto are often made of bronze and it has been observed that during the course of operation thick viscous residues are formed. These residues are akin to tars or gums of a dark brown colour and cannot circulate in the pores of the bearings and thus reduce the free circulation of the oil. This is particularly noticeable in two-layer journal bearings for which loads are higher and porosity finer. It is found in this case that a slow steady increase in the operating temperature occurs in the course of time, this phenomenon being clearly distinct from the abrupt rise in temperature which occurs in the event of seizure.

In order to correct this disadvantage it has already been proposed to make longitudinal grooves forming wells for accumulation of these residues in the bores of the bearings. But the life of the bearing is only multiplied by a factor of 3 to 5, which may be insufficient. It is for this reason that hitherto in the case of journal-bearings or thrust-bearings, intended for operating for a long period of time under high loads, ball or roller members are usually employed in which the lubricant can be renewed. However it is not always possible to give roller or ball bearings the small dimensions which are necessary in certain applications. Additionally, these members are sometimes located in places where it is difficult to ensure renewal of the lubricant.

It is an object of the invention to solve this problem by providing testing methods for achieving self-lubricating journal-bearings having adequate longevity.

Research carried out for this purpose has shown first of all that the deterioration of the oil which has been observed in use of the journal-bearings is influenced by the nature of the material constituting the journal-bearings. Thus it was observed that the oil deteriorated particularly in journal-bearings produced from bronze, this material having been selected because of its antifriction qualities. When iron is employed, better behaviour of the oil is observed. It is therefore proposed that the material constituting the journal-bearing is selected mainly, not as hitherto on its antifriction qualities but on the influence of the material on the quality of the oil employed.

Thus in accordance with one aspect of the invention there is provided a method of testing the qualities of a material for forming at least one portion of a self-lubricating bearing-member containing oil, comprising immersing a quantity of the material reduced to powder in the oil, maintaining the oil at a temperature at most equal to its maximum temperature of use, and verifying that the presence of the material in the oil does not produce in course of time perceptible deterioration of the oil, by comparing the oil with a sample of the same oil kept for the same length of time at the same temperature.

In accordance with another aspect of the invention, there is provided a self-lubricating bearing-member comprising a porous part containing oil, wherein at least one portion of the porous part is formed of a material capable of being immersed in powder form for some tens of hours in the oil kept at its maximum temperature of use without causing perceptible deterioration of the oil.

In a preferred embodiment at least one portion of the self-lubricating bearing-member is obtained by sintering a powder of at least one of the metals of the group formed by molybdenum, iron, lead, silver and nickel.

The invention will be more fully understood from the following description of an embodiment thereof, given by way of example only.

In order to test the qualities of the material which it is desired to employ in a bearing member a predetermined quantity of powder of the material is placed in a cup which is filled with the oil to be employed for lubrication of a journal-bearing made from the material.

Previously the maximum temperature has been determined at which the oil preserves its lubricating qualities. This temperature is generally indicated by the oil supplier. For the oils usually employed, this maximum temperature is of the order of 95° C. The oil covering the material being tested is therefore kept at the selected temperature, for example 95° C, for several hours. At the same time the qualities of this oil are compared with those of the same oil kept at the same temperature but in a cup which does not contain meal powder in suspension.

It is observed that in the presence of certain metals, especially bronze, the oil in course of time takes on a dark brown colour and becomes more viscous. This coincides with the observation that journal bearings produced from bronze and having a load PV = 100 bar.m/s have a rather short life, of the order of 250 hours. On the other hand other metals or alloys affect neither the colouring nor the viscosity of the oil. It has been found that journal-bearings produced from these metals have a long life, e.g. longer than 5000 hours at PV = 100 bar.m/s.

Tests carried out systematically have shown that the following metals or alloys, copper, bronze, manganese, cobalt, monel, bismuth, hasten the deterioration of the oil and should therefore not be selected as the material of self-lubricating journal-bearings, contrary to what had been done hitherto.

On the other hand the following metals, molybdenum, iron, lead, silver, nickel, do not bring about deterioration of the oil and are therefore particularly indicated for the manufacture of self-lubricating thrust-bearings or journal-bearings. As has been indicated, in the above described test the oil is kept at a temperature at most equal to its maximum temperature of use, in order that the test should not be falsified by thermal deterioration of the oil. Furthermore the observations which have been made show clearly that the temperature of the oil does not intervene in the deterioration observed in certain journal-bearings. Thus in a two-layer journal-bearing produced from bronze containing 10% of tin, the working life of which was only 250 hours, the operating temperature did not exceed 65° C during the greater portion of the test. This shows very clearly that the deterioration of the oil under the action of the metal is produced at average temperatures and it should be possible to carry out the test at temperatures lower than the maximum indicated temperature of 95° C. However, deterioration under the action of the metal occurs more rapidly at a relatively high temperature and at these temperatures the reaction of the oil can thus be observed relatively soon, e.g. at the end of some tens of hours. When at the end of a time of the order of 100 hours at 95° C no deterioration of the oil is observed it can be considered that the metal being tested is one of those which do not hasten deterioration of the oil.

The load supported by the journal-bearing and its porosity influence the working life of the bearing since the circulation of the oil is more intense and the microporous layer can get choked more easily. That is why journal-bearings produced from ordinary bronze with fairly large pores and working at low load, or the order of PV = 6 bars.m/s can operate for about 5000 hours at a temperature of 80° C.

The invention is therefore particularly applicable to two-layer journal-bearings working under heavy load, which hitherto had a poor working life because of the selection of the material of which they consisted.

Journal-bearings which consist of a major part of a macroporous material clad with a fine microporous layer favour employment of the method of this invention because it is possible to select a costly metal such as silver to constitute the microporous layer. In a preferred embodiment of this invention a journal-bearing in accordance with the invention is produced in accordance with French Patent No. 1,377,414, which the macroporous portion serving as an oil reservoir being of pure iron and the bore being clad with a thin microporous layer of silver. It has been found that such a journal-bearing operating without addition of oil or an external oil reserve has at a PV = 100 bar.m/s a working life longer than 5000 hours. It was observed at the end of a test on such a bearing that the oil had kept its initial colour and viscosity and was free of thick products of decomposition.

A journal-bearing of this kind combines the advantages of the present invention and of the proposals of Patent No. 1,377,414 since, whilst being able to carry high loads with good lubrication and without risk of entry of air in accordance with the Patent, it has an increased longevity because of the suppression of the risk of clogging of the thin layer. However, the invention is equally applicable to conventional journal-bearings having no thin layer, in particular those which have fine porosity.

In short, whatever the form of the journal-bearing and the dimensions of its pores, selection of the metal in accordance with the above described method enables the longevity of the journal-bearing to be increased due to preservation of the qualities of the oil over a longer period of time.

Among the metals responding to the above described test, those will usually be chosen which are highly resistant to seizure, such as silver and molybdenum. Actually one is never completely secure from accidental seizure and the choice of a material resistant to seizure for constituting the inner layer of the journal bearing is a supplementary guarantee of longevity. But this is a question of a supplementary advantage and the decisive criterion in the choice of metal will be that of not changing the nature of the oil. Furthermore, as it was found by a test in accordance with the invention that nickel is one of the metals which do not affect the qualities of the oil, two-layer journal-bearings have been produced having an outer macroporous portion of iron clad internally with a microporous layer of nickel. A journal-bearing of this kind has operated at a PV of 120 bars.m/s for more than 1000 hours. This clearly shows that anti-friction properties are added to those obtained by use of the invention since a journal-bearing produced from a metal as well known as nickel for the risk of accidental seizure profits, however, by a longevity 4 times better than that obtained by a journal-bearing of bronze, the alloy chosen hitherto for its anti-friction properties.

Of course the invention is not intended to be limited to the details of the embodiments which have just been described but embraces all variants, and especially those which might differ from them only by the use of equivalent means, within the scope of the invention. Thus while a certain number of metals have been mentioned which satisfy the criteria of choice previously defined this list is not exclusive; similarly the duration of the tests and the temperatures have been given by way of example only because they correspond to the oils usually employed.

Finally, while the invention has been particularly described and tests have been performed particularly for journal-bearings, but it will be appreciated that the method can be employed for selecting the materials constituting any self-lubricating member in which the movement of the shaft or a bearing part causes circulation of the oil, especially thrust-bearings.

What is claimed is:

1. A method of testing the qualities of a porous material for forming at least one portion of a self-lubricating bearing-member containing oil, said method comprising immersing a quantity of said material reduced to powder form in said oil, maintaining said oil at a temperature at most equal to its maximum temperature of use for a period of time of tens of hours, separately maintaining at said temperature and for the same period of time a sample of the same oil without the powder material immersed therein, and verifying that the presence of said powder material in said oil does not produce in the course of said time period perceptible deterioration of the oil, by comparing said oil with the sample of the same oil kept for the same period of time at the same temperature whereby the powder material can be determined as suitable for use as the porous material of the self-lubricating bearing member.

2. A method as claimed in claim 1, wherein said oil is maintained at a temperature of the order of 95° C.

3. A method as claimed in claim 1, wherein said material is immersed in said oil for at least 100 hours.

4. A method as claimed in claim 1, wherein it is verified that the presence of said material in said oil does not perceptibly affect the colouring or the viscosity of said oil.

5. A method as claimed in claim 1, wherein it is verified that the presence of said material in said oil does not cause the appearance of thick products in the oil.

6. A method as claimed in claim 1, wherein said material is at least one metal selected from the group consisting of molybdenum, iron, lead, silver, and nickel.

7. A method as claimed in claim 1, wherein said material is capable of being immersed for at least 100 hours in said oil kept at 95° C without causing abnormal variation in the colouring and viscosity of said oil.

* * * * *